United States Patent
Venderbosch et al.

(10) Patent No.: US 11,629,117 B2
(45) Date of Patent: Apr. 18, 2023

(54) ESTERS OF AMINO CARBOXYLIC ACIDS AND A PROCESS TO PREPARE THEM

(71) Applicant: NOURYON CHEMICALS INTERNATIONAL B.V., Arnhem (NL)

(72) Inventors: Rudolf Antonius Maria Venderbosch, Duiven (NL); Alexander Michael Wetzel, Jörlanda (SE); Louis Eckhard Schwarzmayr, Hjälteby (SE); Hanna Ingrid Birgitta Jacobson Ingemyr, Frölunda (SE); Natalija Smolko Schwarzmayr, Hjälteby (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 17/250,265

(22) PCT Filed: Jul. 1, 2019

(86) PCT No.: PCT/EP2019/067539
§ 371 (c)(1),
(2) Date: Dec. 22, 2020

(87) PCT Pub. No.: WO2020/007774
PCT Pub. Date: Jan. 9, 2020

(65) Prior Publication Data
US 2021/0114971 A1   Apr. 22, 2021

(30) Foreign Application Priority Data

Jul. 3, 2018 (EP) .................. 18181480

(51) Int. Cl.
*C07C 227/22* (2006.01)

(52) U.S. Cl.
CPC ............... *C07C 227/22* (2013.01)

(58) Field of Classification Search
None
See application file for complete search history.

(56) References Cited

U.S. PATENT DOCUMENTS

| | | | |
|---|---|---|---|
| 3,211,781 A | 10/1965 | Taub et al. | |
| 3,567,763 A * | 3/1971 | Emmons | C07C 265/04 560/129 |
| 3,939,200 A * | 2/1976 | Emmons | C08G 18/771 560/155 |
| 4,216,227 A | 8/1980 | Cook et al. | |

FOREIGN PATENT DOCUMENTS

| | | | |
|---|---|---|---|
| EP | 0847987 A1 | 6/1998 | |
| JP | S49082624 A | 8/1974 | |
| WO | WO-2019110371 A1 * | 6/2019 | ............... C11D 1/22 |

OTHER PUBLICATIONS

Pubchem entry of 2-ethylhexanol: https://pubchem.ncbi.nlm.nih.gov/compound/2-Ethylhexanol#section=Boiling-Point&fullscreen=true, downloaded on Aug. 20, 2021 (Year: 2021).*
PubChem entry for n-butanol: downloaded from https://pubchem.ncbi.nlm.nih.gov/compound/1-Butanol#section=Boiling-Point&fullscreen=true on Aug. 23, 2021 (Year: 2021).*
PubChem entry for n-hexanol: downloaded from https://pubchem.ncbi.nlm.nih.gov/compound/1-Hexanol on Aug. 23, 2021 (Year: 2021).*
Water-1-Hexanol Azeotropic Data: https://materials.springer.com/thermophysical/docs/azd_c174c296, downloaded on Aug. 23, 2021 (Year: 2021).*
Wikipedia entry for "2-Ethylhexanol", downloaded from https://en.wikipedia.org/wiki/2-Ethylhexanol on Jan. 24, 2022 (Year: 2022).*
Sigma-Aldrich web catalogue page for "2-Ethyl-1-hexanol", downloaded from https://www.sigmaaldrich.com/US/en/product/aldrich/538051 on Jan. 24, 2022 (Year: 2022).*
"1-Hexanol", downloaded from https://pubchem.ncbi.nlm.nih.gov/compound/8103#section=Boiling-Point&fullscreen=true on Jan. 24, 2022. (Year: 2022).*
EPO, European Extended Search Report issued in EP Application No. 18181480.7, dated Jan. 14, 2019.
EPO, International Search Report issued in IA No. PCT/EP2019/067539, dated Sep. 10, 2019.
Klimentova, J., et al. "Transkarbams with terminal branching as transdermal permeation enhancers", Biorganic & Medicinal Chemistry Letters, Mar. 1, 2008, pp. 1712-1715, vol. 18, No. 5.
Hrabálek, A., et al. "Esters of 6-aminohexanoic acid as skin permeation enhancers: The effect of branching in the alkanol moiety", Journal of Pharmaceutical Sciences, Jul. 7, 2005, pp. 1494-1499, vol. 94, No. 7.

* cited by examiner

*Primary Examiner* — Amy C Bonaparte
(74) *Attorney, Agent, or Firm* — Lorenz & Kopf, LLP

(57) ABSTRACT

The present disclosure relates to a process to prepare esters of an amino carboxylic acid of the formula (I) comprising the steps of reacting an aminocarboxylic acid present as a cyclic amide of the formula II and an alkanol of the formula R—(O-A)mOH in the presence of the Brønsted-Lowry acid at a temperature of between 60 and 200 degrees C. wherein the total molar amount of aminocarboxylic acid to the molar amount of the alkanol is between 1:0.8 and 1:1.5 and wherein the Brønsted-Lowry acid is not added to the reaction mixture until least 50% of the total of the alkanol and cyclic amide are added to the reaction mixture.

8 Claims, No Drawings

ESTERS OF AMINO CARBOXYLIC ACIDS AND A PROCESS TO PREPARE THEM

CROSS-REFERENCE TO RELATED APPLICATION

This application is a U.S. National-Stage entry under 35 U.S.C. § 371 based on International Application No. PCT/EP2019/067539, filed Jul. 1, 2019, which was published under PCT Article 21(2) and which claims priority to European Application No. 18181480.7, filed Jul. 3, 2018, which are all hereby incorporated in their entirety by reference.

TECHNICAL FIELD

The present disclosure relates to a process to prepare esters of amino carboxylic acids and esters obtainable by such process.

BACKGROUND

A process to prepare esters of aminocarboxylic acids is disclosed in "Esters of 6-aminohexanoic acid as skin permeation enhancers: The effect of branching in the alkanol moiety", A Habralek et al, Journal of Pharmaceutical Sciences, Vol. 94, 1494-1499, (2005). The process disclosed in this document involves in a first step a conversion of the amino carboxylic acid to an amino acyl chloride that next reacts with an alkanol to give an ammonium functional ester that next is deprotonated to give the aminocarboxylic acid ester.

JP S49-082624 discloses a process to prepare esters of aminocarboxylic acids in which an aminocarboxylic acid or a cyclic amide thereof is first reacted with a mineral acid catalyst which will convert this aminocarboxylic acid or cyclic amide into its aminocarboxylic acid salt, and next this aminocarboxylic acid salt is esterified with an alkanol to give the ester of the alkanol and the aminocarboxylic acid. This process is hence an esterification (or condensation) reaction, in embodiments wherein the cyclic amide precursor is employed, preceded by a de-esterification (or hydrolysis) reaction. The process is done at a temperature of 150 deg C. and the alkanol reactant is 20% overdosed on cyclic amide molar amount.

J Klimentova, et al, in "Transkarbams with terminal branching as transdermal permeation enhancers", Bioorganic & Medicinal Chemistry Letter 18 (2008), 1712-1715 disclose also an esterification reaction of the salt of an aminocarboxylic acid with an alkanol in the presence of thionylchloride. The molar ratio of aminocarboxylic acid salt to alkanol in this document is 6.16:5.54 which corresponds with 1.11:1.00.

U.S. Pat. No. 4,216,227 discloses a process to prepare omega amino acid esters by reacting omega amino acid salts with an excess of alkanol in the presence of dry HCl gas. The details of the process are not disclosed, other than that a temperature of 150 deg C. is employed for 3 hours, and neither is the use of cyclic amide instead of amino acid salt disclosed.

EP 847987 also discloses a process to prepare esters of aminocarboxylic esters. The process disclosed in EP 987 involves reacting an aminocarboxylic acid or a cyclic amide thereof with an alkanol in the presence of a divalent or trivalent inorganic acid, wherein the alkanol is dosed in high molar excess relative to the amount of the aminocarboxylic acid and later distilled off. The process is said to be performed under reflux conditions for several hours.

U.S. Pat. No. 3,211,781 like EP 847987, discloses a process to prepare esters of amino carboxylic acids wherein a cyclic amide of an amino carboxylic acid is reacted with an alkanol in the presence of a Brønsted-Lowry acid under reflux conditions. Also, in this document the alkanol is dosed in a high molar excess compared to the molar amount of cyclic amide.

BRIEF SUMMARY

This disclosure provides a process to prepare esters of an amino carboxylic acid of the formula (I)

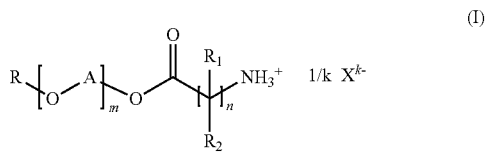

wherein R is an alkyl group comprising 5 to 16 carbon atoms that may be branched or linear, k is a value of 1 to 3, m is an integer from 0 to 25, A is —CH2-CH2- or —CH2CH(CH3)- or —CH2-CH(CH2-CH3)-, n is an integer of at least 3 and at most 8, each R1 is a hydrogen atom, each R2 is independently a hydrogen atom or methyl or ethyl group, and wherein X is an anion derivable from deprotonating a Brønsted-Lowry acid comprising the steps of reacting an aminocarboxylic acid present as a cyclic amide of the formula II

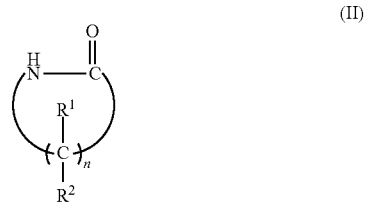

and an alkanol of the formula R—(O-A)mOH in the presence of the Brønsted-Lowry acid at a temperature of between 60 and 200 degrees C. wherein the total molar amount of aminocarboxylic acid to the molar amount of the alkanol is between 1:0.8 and 1:1.5 and wherein the Brønsted-Lowry acid is not added to the reaction mixture until least 50% of the total of the alkanol and cyclic amide are added to the reaction mixture.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has been found that a process to prepare esters of aminocarboxylic acids can also be performed by dosing the alkanol and the cyclic amide of aminocarboxylic acid in similar molar amounts so that the alkanol does not have to be distilled off and furthermore that the transesterification reaction when performing the process in this way can be catalyzed by many Brønsted-Lowry acids, also monovalent acids.

The advantage of performing a transesterification reaction of a cyclic amide of an amino carboxylic acid instead of an esterification of an amino carboxylic acid or salt thereof is that it is much easier to control the amount of water in the process. When doing a transesterification reaction there is no net formation of water. When performing an esterification reaction, more water will form and such increased water content may give rise to side reactions, such as in particular under an acidic pH, a hydrolysis reaction wherein formed product falls apart in the starting compounds again. Also, when attempting to remove water from the reaction mixture, the reactants, most notably the alkanols, might form an azeotrope with the water and get lost as well.

Furthermore, it has been found that the side reaction wherein the cyclic amide self-polymerizes that is suppressed in state of the art processes by diluting the reaction mixture with an excess of alkanol reactant was found to be similarly suppressed in the process as contemplated herein, wherein the reactants cyclic amide and alkanol are dosed equimolar, or close to equimolar, especially in embodiments wherein the process is done under somewhat more moderate temperatures, such as temperatures under 150 deg C. Quite unexpectedly, in the process as contemplated herein the (trans)esterification reaction takes similarly long as in the prior art processes wherein the alkanol is clearly overdosed and still very similar yields of desired product are obtained. Finally, it is an advantage that the excess of alkanol does not need to be removed from the reaction mixture.

The present disclosure now provides an improved process to prepare esters of an amino carboxylic acid of the formula (I)

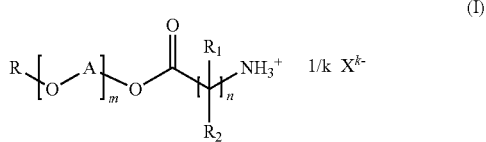

wherein R is an alkyl group containing 5 to 16 carbon atoms that may be branched or linear, k is a value of 1 to 3, m is an integer from 0 to 25, each A independently is —CH2-CH2- or —CH2CH(CH3)- or —CH2-CH(CH2-CH3)-, n is an integer of at least 3 and at most 8, each R1 is a hydrogen atom, each R2 is independently a hydrogen atom or methyl or ethyl group, preferably each R2 is a hydrogen atom, and wherein X is an anion derivable from deprotonating a Brønsted-Lowry acid comprising the steps of reacting a cyclic amide of the formula II

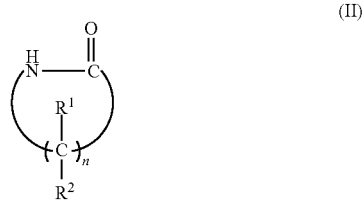

and an alkanol of the formula R—(O-A)mOH in the presence of a Brønsted-Lowry acid at a temperature of between 60 and 200 degrees C. wherein the total molar amount of cyclic amide to the molar amount of the alkanol is between 1:0.8 and 1:1.5 and wherein the Brønsted-Lowry acid is not added to the reaction mixture until at least 50% of the total of the alkanol and cyclic amide are dosed.

The disclosure furthermore provides esters of amino carboxylic acids of the formula (I) as obtainable by the process as contemplated herein.

More Preferred Esters Include 6-aminobutanoic acid 2-ethylhexan-1-yl ester sulphate, 6-aminobutanoic acid 2-ethylhexan-1-yl ester chloride, 6-aminobutanoic acid 2-ethylhexan-1-yl ester hydrogen sulphate, 6-aminobutanoic acid 2-ethylhexan-1-yl ester phosphate, 6-aminobutanoic acid isodecan-1-yl ester sulphate, 6-aminobutanoic acid isodecan-1-yl ester chloride, 6-aminobutanoic acid isodecan-1-yl ester hydrogen sulphate, 6-aminobutanoic acid isodecan-1-yl ester phosphate, 6-aminohexanoic acid isodecan-1-yl ester sulphate, 6-aminohexanoic acid isodecan-1-yl ester chloride, 6-aminohexanoic acid isodecan-1-yl ester hydrogen sulphate, 6-aminohexanoic acid isodecan-1-yl ester phosphate, 6-aminohexanoic acid 2-ethylhexan-1-yl ester sulphate, 6-aminohexanoic acid 2-ethylhexan-1-yl ester chloride, 6-aminohexanoic acid 2-ethylhexan-1-yl ester hydrogen sulphate, and 6-aminohexanoic acid 2-ethylhexan-1-yl ester phosphate.

The compounds of formula (I) were determined to be readily biodegradable, which adds to the environmental profile of any application in which they are used.

In the process as contemplated herein the cyclic amide derivative of formula (II), and the alkanol are preferably employed in a molar ratio of total cyclic amide of formula (II) to alkanol that is typically between 1:0.8 and 1:1.3, more typically between 1:0.9 and 1:1.1, most typically both compounds are used in a substantially equimolar amount.

Unexpectedly the reaction can be performed under relatively mild conditions such as a milder reaction temperature, and provide high yields of the ester if the alkanol is used in the ratio of the present disclosure. Effectively the reaction was found to progress substantially towards the claimed ester product in which there is only a limited remaining amount of unreacted alkanol and cyclic amide and in which only found trace amounts of only one side product that is the reaction product of alkanol and Brønsted-Lowry acid are found.

In applications wherein a considerable amount of alkanol or side products caused by not being able to control the amount of water, create a problem but a minor amount of unreacted alkanol or cyclic amide are not an issue, the product of the process as contemplated herein can be used without intermediate steps to remove impurities such as for example unreacted starting materials.

As indicated, the Brønsted-Lowry acid is not added to the reaction mixture until at least 50% of the total of the alkanol and at least 50% of the total of the cyclic amide of the aminocarboxylic acid are added. In a preferred embodiment at least 75% of the total of the alkanol and at least 75% of the cyclic amide are dosed before the Brønsted-Lowry acid is added to the reaction mixture, even more preferably at least 90%. In a preferred embodiment, at least part of the alkanol is first dosed to the reactor and next at least part of the cyclic amide, after which the Brønsted-Lowry acid is added. It however is also possible to dose the cyclic amide partially or completely before the alkanol is dosed to the reactor or to simultaneously dose the cyclic amide and the alkanol after which the Brønsted-Lowry acid is added.

The temperature is preferably increased to at least 60 deg C. and to up to 200 deg C. after the reactants and the Brønsted-Lowry acid have been dosed. It is beneficial to first increase the temperature to between 60 and 100 deg C. and next to a temperature between 100 and 150 deg C., or even more typically 110 and 140 deg C.

The process can be performed in a solvent or without a solvent. The process is preferably performed with an amount of solvent that is 0 to 10 wt % based on total reactants. If a solvent is used it is preferably a non-alcoholic organic solvent with a boiling point of at least 100 deg C., or water.

In a preferred embodiment the molar amount of water on total moles of cyclic amide is between 0 and 10 mole %, more typically 0.01 and 5 mole %, most typically 0.1 and 2 mole %.

After the reaction is completed, optionally (to decrease viscosity) the product can be diluted with organic solvent. The preferred organic solvents are glycolic solvents, such as propylene glycol, triethylene glycol, ethylene glycol, 2-methoxyethanol, glycerol, or isopropanol.

The Brønsted-Lowry acid is preferably used as a concentrated (i.e. 20 to 100 wt %) aqueous solution and dosed to the reaction mixture containing all the cyclic amide and the alkanol in portions to control the exothermal effect of the reaction.

The Brønsted-Lowry acid is not an aminocarboxylic acid. The Brønsted-Lowry acid is preferably an acid with a pKa of between −10 and 3. The Brønsted-Lowry acid is even more preferably an inorganic acid, even more preferably it is sulfuric acid, phosphoric acid or a hydrohalic acid and most preferably it is sulfuric acid as hydrohalic acids such as HCl in embodiments result in solid products and phosphoric acid results in lower conversions. Moreover both HCl and $H_3PO_4$ are available as aqueous solutions (HCl 37% conc, $H_3PO_4$ 85% conc) while $H_2SO_4$ is available in substantially water-free form (such as 95-98% concentrate). The use of $H_2SO_4$ therefore allows to get products of high conversion (>90%) in a liquid form, and moreover no need to evaporate water exists.

X is in a preferred embodiment an anion derived from an inorganic Brønsted-Lowry acid, more preferred a halogenide, sulphate, hydrogen sulfate, hydrogen phosphate, dihydrogen phosphate, or phosphate anion The process can be done under reduced pressure but is preferably performed at a pressure that is atmospheric.

The product can optionally be neutralized by a base to a pH from 4-7. The product can be purified by methods available to someone skilled in the art. However, because of the low level of side products, it can also be used without further processing or purification steps, such as a surfactant.

In a preferred embodiment R is an alkyl group of 6 to 16 carbon atoms. In a more preferred embodiment R is an alkyl group that contains 8 to 13 carbon atoms. In another preferred embodiment R is branched on the carbon atom beta from the oxygen atom. In further embodiments R can contain more than a single branched carbon atom.

The process is very favorable for alkanols that have a boiling point up to 220 deg C., or, for alkanols that can form an azeotrope with water having a boiling point lower than 220 deg C. Compared to the state of the art processes, in the process as contemplated herein when using such alkanols, they will not be stripped from the reaction mixture when reaction water is removed, as in the process as contemplated herein no such water is formed and hence does not need to be removed. Many alkanols that can be used in the process as contemplated herein have a boiling point in this range (especially the alkanols that are smaller or that contain some branching in their structure).

It should be noted that a mixture of alkanols can also be employed in the process.

It is furthermore preferred that n is 4, 5 or 6.

The process is typically done at a temperature of between 60 and 150 deg C., more preferably between 80 and 145 deg C., most typically 110 and 140 deg C.

EXAMPLES

Compounds Used
ε-Caprolactam (ex Acros Organics)
pyrrolidone (ex Acros Organics)
2-ethylhexanol (ex Perstorp)
Isodecanol (ex Exxon)
HCl (ex Merck)
$H_3PO_4$ (85%) (ex Fisher scientific)
$H_2SO_4$ (95%) (ex VWR)

Example 1— preparation of 6-aminohexanoic acid ethylhexan-1-yl ester salt

2-Ethylhexanol was added to a round bottom flask and dried on a rotavapor at 70° C. for 3 hours (water content 0.049%). Caprolactam (114 g; 1.01 mol) and pre dried 2-Ethylhexanol (131.18 g; 1.01 mol) were added to a 250-mL glass reactor fitted with a thermometer, a heating mantel and a mechanical stirrer. The reaction mixture was heated to 60-65° C. for a homogeneous reaction mixture. Concentrated aqueous hydrochloric acid (HCL (conc 37%, 99 g; 1 mol)) was added dropwise to the reaction mixture and showed a small exotherm. The temperature was increased to 140° C. The reaction was stopped after 12 hours.

The product was isolated and analyzed by $^1H$ NMR. 70% conversion of the aminocarboxylic acid and alkanol to the desired alkyl-6-aminohexanoate was established.

Example 2— preparation of 6-aminohexanoic acid 2-ethylhexan-1-yl ester sulphate

The above Example 1 was repeated, however now 90 wt % aq. sulfuric acid ($H_2SO_4$, 54.9 g; 0.504 mol) was used instead of hydrochloric acid.

The product was isolated and analyzed by NMR to have been obtained with 85% conversion.

Example 3— Preparation of 6-aminohexanoic acid 2-ethylhexan-1-yl ester sulphate

The above Example 2 was repeated, however now 95 wt % aq. sulfuric acid ($H_2SO_4$, 52 g; 0.504 mol) was used instead of 90 wt % aq. sulfuric acid.

The product was isolated and analyzed by NMR to have been obtained with 88% conversion.

Example 4— Preparation of 6-aminohexanoic acid 2-ethylhexan-1-yl ester sulphate

The above Example 3 was repeated, however now 10% excess of caprolactam (125.4 g; 1.111 mol) and $H_2SO_4$ (57.5 g; 0.56 mol) were used.

The product was isolated and analyzed by NMR to have been obtained with 92% conversion.

Example 5— Preparation of 6-aminohexanoic acid isodecan-1-yl ester sulphate

The above Example 2 was repeated, however now instead of 2-ethylhexanol as the alkanol, isodecanol was used (159.43 g, 1.01 mol).

The product was isolated and analyzed by NMR to have been obtained with 86% conversion.

Example 6— Preparation of 6-aminohexanoic acid 2-ethylhexan-1-yl ester phosphate Example 1 was repeated however now instead of hydrochloric acid, phosphoric acid H3PO4 (85%, 34.1 g; 0.296 mol) was used as the acid.

The product was obtained with 31% conversion.

Example 7— Preparation of 6-aminobutanoic acid 2-ethylhexan-1-yl ester sulphate

The above Example 3 was repeated, however now pyrrolidin-2-one (85.96; 1.01 mol) was used instead of caprolactam.

The product was isolated and analyzed by NMR to have been obtained with 53% conversion.

Comparative Example 8— Preparation of 6-aminohexanoic acid isodecan-1-yl ester sulphate according to state of the art process The procedure as described in JP S49-082624 was followed:
A 500 mL flanged glass reactor with overhead stirrer, thermometer and cooler was loaded with ε-caprolactam (66 g, 0.58 mol) and hydrochloric acid (18% in water, 177 g, 0.88 mol). The mixture was heated to 110 deg C. for three hours. Then, 2-ethylhexanol (91 g, 0.70 mol) was added and the mixture was heated to 150 deg C. The cooler was removed and a gentle nitrogen stream was applied to the system for eight hours. When leaving the vessel, the nitrogen stream was directed into a gas washing bottle with aq. NaOH (20%, 200 ml). Finally, the mixture was cooled to room temperature and analysed by NMR. The product was obtained as a white solid (81 g, 50%).

In the Examples 1 to 7 ε-caprolactam becomes activated by the acid to initiate ring-opening by 2-ethylhexanol, the reaction in the Comparative Example 8 is based on a two-step mechanism. In the latter process, caprolactam becomes opened by water and acid producing 6-aminohexanoic acid in salt form, which then subsequently undergoes a condensation with the alcohol in a second step. The intermediate 6-aminohexanoic acid is formed virtually quantitative as verified by NMR. Afterwards, addition of the alcohol and heating to 150 deg C. initiates a condensation reaction. In the Examples 2 to 4, ε-caprolactam, 2-ethylhexanol and concentrated sulfuric acid were mixed at temperatures below 70 deg C.

The product formation in the Examples 1 to 7 is based on a ring-opening reaction by the alcohol in a closed vessel (i.e. a transesterification) rather than a condensation reaction (a hydrolysis followed by a condensation). The different mechanism has a tremendous influence on the outcome of the reaction. Especially, the last step in Comparative Example 8 requires high temperatures and water stripping which result in a lower yield, even more so when using alcohols with boiling points lower than 220 deg C. that will be stripped off with the water. It was noticed that large quantities of 2-ethylhexanol were stripped off at 150 deg C. together with water through the nitrogen stream due to the boiling point of 2-ethylhexanol being 184 deg C., and some azeotrope formation. A total yield of 50% of product resulted, which is low compared to the Examples 1 to 7.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process to prepare an ester, said method comprising the steps of:
   reacting via ring-opening alcoholysis:
      a cyclic amide chosen from caprolactam, pyrrolidine-2-one, and combinations thereof, and
      an alkanol chosen from 2-ethylhexanol, isodecanol, and combinations thereof,
      in the presence of a Brønsted-Lowry acid chosen from hydrochloric acid, sulfuric acid, phosphoric acid, and combinations thereof,
      at a temperature of between 60 and 200° C.,
   wherein the molar ratio of the alkanol to the Brønsted-Lowry acid is from about 1.01:0.3 to about 1.01:1,
   wherein the total molar amount of cyclic amide to the molar amount of the alkanol is between 1:0.9 and 1:1.1,
   wherein the Brønsted-Lowry acid is not added to the cyclic amide and/or alkanol until at least 50% of the total of the alkanol and cyclic amide are combined,
   wherein the cyclic amide and the alkanol are combined before addition of the Brønsted-Lowry acid such that a molar amount of water present in the combination to the total moles of cyclic amide in the combination is between about 0 and about 2 mole %; and
   wherein the process is free of an organic solvent.

2. Process of claim 1 wherein the cyclic amide is caprolactam, the alkanol is 2-ethylhexanol, and the Brønsted-Lowry acid is hydrochloric acid.

3. Process of claim 1 wherein the cyclic amide is caprolactam, the alkanol is 2-ethylhexanol, and the Brønsted-Lowry acid is sulfuric acid.

4. Process of claim 1 wherein the cyclic amide is caprolactam, the alkanol is isodecanol, and the Brønsted-Lowry acid is sulfuric acid.

5. Process of claim 1 wherein the cyclic amide is caprolactam, the alkanol is 2-ethylhexanol, and the Brønsted-Lowry acid is phosphoric acid.

6. Process of claim 1 wherein the cyclic amide is pyrrolidine-2-one, the alkanol is 2-ethylhexanol, and the Brønsted-Lowry acid is sulfuric acid.

7. Process of claim 1 wherein the cyclic amide is caprolactam, the alkanol is or 2-ethylhexanol, and the Brønsted-Lowry acid is hydrochloric acid.

8. Process of claim 5 wherein the total molar amount of caprolactam to the molar amount of the or 2-ethylhexanol is about 1:1.

* * * * *